United States Patent [19]

Turk

[11] Patent Number: 5,554,180
[45] Date of Patent: Sep. 10, 1996

[54] INTRALUMINAL STENTING GRAFT

[75] Inventor: Rodney E. Turk, West Bloomfield, Mich.

[73] Assignee: Aeroquip Corporation, Maumee, Ohio

[21] Appl. No.: 499,740

[22] Filed: Jul. 7, 1995

[51] Int. Cl.$^6$ ............................................. A61F 2/04
[52] U.S. Cl. ........................ 623/1; 623/12; 606/194; 606/198
[58] Field of Search ................. 623/1, 11, 12; 606/108, 191, 194, 195, 198; 604/96, 104, 281

[56] References Cited

U.S. PATENT DOCUMENTS

| | | | |
|---|---|---|---|
| 4,195,623 | 4/1980 | Zeff et al. | 128/273 |
| 4,195,637 | 4/1980 | Gruntzig et al. | 128/348 |
| 4,271,839 | 6/1981 | Fogarty et al. | 128/344 |
| 4,386,601 | 6/1983 | Trick | 128/346 |
| 4,508,112 | 4/1985 | Seeler | 128/89 R |
| 4,577,631 | 3/1986 | Kreamer | 623/1 |
| 4,649,914 | 3/1987 | Kowalewski | 128/207.15 |
| 4,733,665 | 3/1988 | Palmaz | 623/1 |
| 4,739,762 | 4/1988 | Palmaz | 623/1 |
| 4,740,207 | 4/1988 | Kreamer | 623/1 |
| 4,762,130 | 8/1988 | Fogarty et al. | 128/344 |
| 4,769,029 | 9/1988 | Patel | 623/1 |
| 4,774,949 | 10/1988 | Fogarty | 128/4 |
| 4,776,337 | 10/1988 | Palmaz | 623/1 |
| 4,787,899 | 11/1988 | Lazarus | 623/1 |
| 4,793,348 | 12/1988 | Palmaz | 128/325 |
| 4,795,458 | 1/1989 | Regan | 623/1 |
| 4,877,025 | 10/1989 | Hanson | 128/207.16 |
| 4,955,895 | 9/1990 | Sugiyama et al. | 606/194 |
| 5,102,417 | 4/1992 | Palmaz | 606/195 |
| 5,156,620 | 10/1992 | Pigott | 623/1 |
| 5,192,311 | 3/1993 | King et al. | 623/1 |
| 5,330,528 | 7/1994 | Lazim | 623/1 |
| 5,464,419 | 11/1995 | Glastra | 606/194 |

OTHER PUBLICATIONS

"Design of an Inflatable Endovascular Aortic Prosthesis", J. P. Pigott, H. G. Beebe, Jobst Vascular Center, Toledo, Ohio, 1 page.

Primary Examiner—Randy C. Shay
Attorney, Agent, or Firm—Emch, Schaffer, Schaub & Porcello Co., L.P.A.

[57] ABSTRACT

An intraluminal stenting graft for implantation in a blood vessel including a collapsible tube member having a first end and a second end. The tube member further includes an outer layer and an inner layer extending between the ends. The outer layer is joined to the inner layer to form a plurality of cylinders extending longitudinally between the first end and the second end. The cylinders provide structural support to the tube member. An absorbent is positioned in at least one of the cylinders. When an absorbate is introduced to the plurality of cylinders and the absorbent, the absorbent absorbs the absorbate. The absorbent increases in volume as a result of such absorption to support the collapsible tube member at the site of implantation of the intraluminal stenting graft in a blood vessel.

13 Claims, 2 Drawing Sheets

INTRALUMINAL STENTING GRAFT

BACKGROUND OF THE INVENTION

The present invention is directed to an intraluminal stenting graft for implantation in a blood vessel. More specifically, the invention is directed to an intraluminal stenting graft that contains an absorbent that when introduced to an absorbate can increase in volume to support the stenting graft at the site of implantation.

Intraluminal stenting grafts are known in the art. Many of these prior art stenting grafts are comprised of substances that are not biocompatible. This can cause health problems in a patient whose blood vessel is being exposed to the stenting graft. Therefore, there is a need for an intraluminal stenting graft that is comprised on materials that are biocompatible. The present invention satisfies this need.

SUMMARY OF THE INVENTION

The present invention is directed to an intraluminal stenting graft for implantation in a blood vessel. The stenting graft includes a collapsible tube member having a first end and a second end. The tube member further includes an outer layer and an inner layer extending between the ends. The outer layer is joined to the inner layer to form a plurality of cylinders extending longitudinally between the first end and the second end. The cylinders provide structural support to the tube member. An absorbent is positioned in at least one of the cylinders.

When an absorbate is introduced to the plurality of cylinders and the absorbent, the absorbate causes the collapsible tube member to expand and the absorbent absorbs the absorbate. The absorbent increases in volume as a result of such absorption to support the expanded tube member at the site of implantation of the intraluminal stenting graft in a blood vessel.

The primary object of the present invention is to provide an intraluminal stenting graft that is biocompatible.

An important object of the present invention is to provide an intraluminal stenting graft that provides superior support for a blood vessel.

Other objects and advantages of the invention will become apparent upon a review of the accompanying drawings and the following detailed description of the invention.

DETAILED DESCRIPTION OF THE PREFERRED EMBODIMENT

Figure 1:
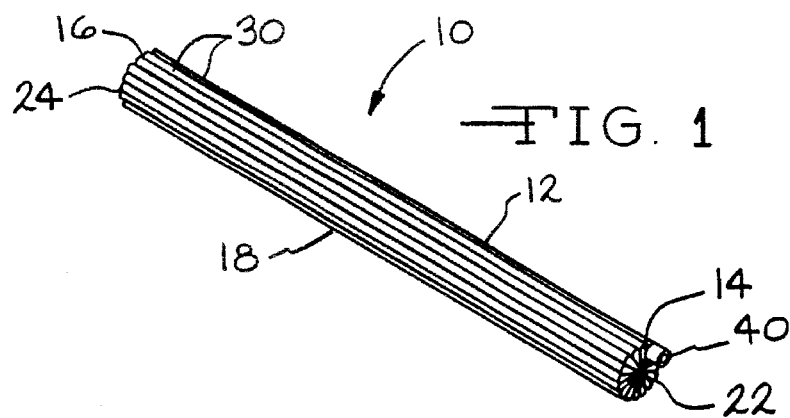
FIG. 1 is a perspective view of an intraluminal stenting graft according to the present invention showing the collapsible tube member in a collapsed state.
Figure 2:
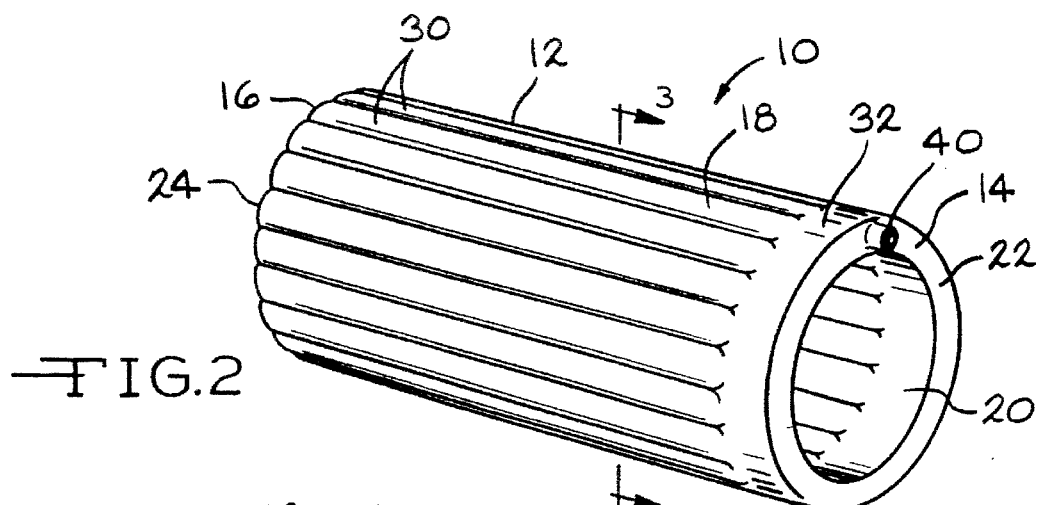
FIG. 2 is a perspective view of an intraluminal stenting graft according to the present invention showing the collapsible tube member in an expanded state.
Figure 3:
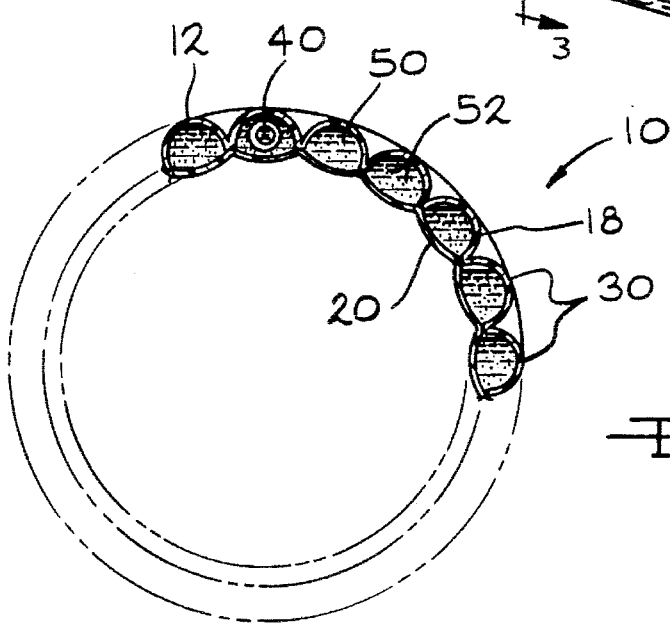
FIG. 3 is a cross-sectional view taken along line 3—3 of FIG. 2 showing an absorbent positioned in the plurality of cylinders with an absorbate.

The present invention will now be described in detail with reference being made to the drawings. Referring to FIGS. 1, 2 and 3, the intraluminal stenting graft of the present invention is indicated by the reference number 10. The stenting graft 10 includes a collapsible tube member 12 having a first end 14 and a second end 16. An outer layer of material 18 and an inner layer of material 20 extend between the first end 14 and the second end 16. A first end wall 22 extends between the outer layer 18 and the inner layer 20 at the first end 14. A second end wall 24 extends between the outer layer 18 and the inner layer 20 at the second end 16.

As shown in FIGS. 1, 2 and 3, the outer layer 18 is joined to the inner layer 20 to form a plurality of cylinders 30 that extend longitudinally between the first end 14 and the second end 16. As shown in FIG. 2, the tube member 12 can include a circumferentially extending chamber 32 that is in communication with the plurality of cylinders 30. In the present embodiment, the chamber 32 is positioned adjacent the first end 14. However, it should be understood that the chamber 32 can be positioned in a variety of locations along the length of the tube member 12.

Figure 5:
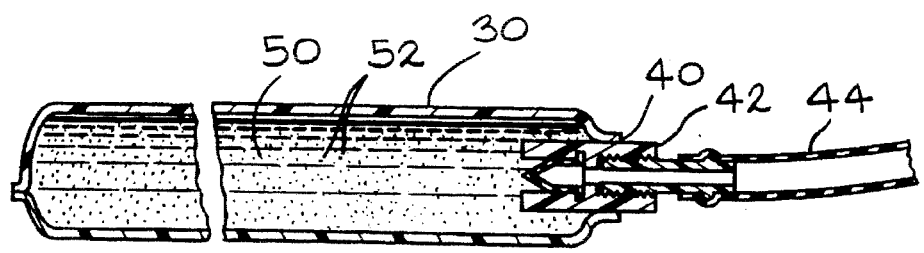
FIG. 5 is a cross-sectional view through the center of the one-way valve of the present invention positioned in an opening of an end wall of the tube member as an absorbate is being introduced to the absorbent.
Figure 6:
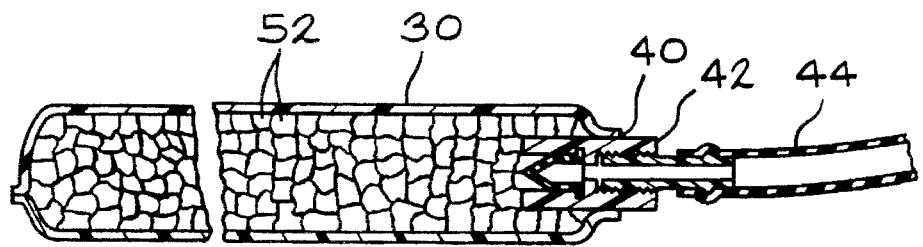
FIG. 6 is a view similar to the view of FIG. 5 showing the absorbent after absorption of the absorbate.

Referring to FIGS. 1, 2 and 3, the tube member 12 can include an opening 40 in the first end wall 22. The opening 40 provides access to the interior of the tube member 12. As shown in FIGS. 5 and 6, a valve, such as a one-way check valve 42, can be positioned in the opening 40. The valve 42 allows for the introduction of substances into the tube member 12. The valve prevents the escape of the substances from the tube member 12 after introduction into the tube member. The substances can be introduced into the tube member 12 through the valve 42 by a conduit 44.

Referring to FIG. 2, the outer layer 18 and the inner layer 20 are composed of a polymer material that is biocompatible. An example of such a material is polytetrafluoroethylene. The outer layer 18 is constructed of a more flexible or lighter weight material than the inner layer 20. This allows the outer layer 18 to be more compliant when the tube member 12 is expanded. The inner layer 20 can be treated or coated with a material such as an expanded polytetrafluoroethylene to create a surface more conducive to blood flow.

An absorbent is positioned in the cylinders 30 of the tube member 12. The absorbent should be capable of absorbing a large quantity of an absorbate, such as a fluid. Preferably, small amounts of the absorbent should be used in order to maintain a small insertion diameter of the tube member 12 as shown in FIG. 1. The absorbent can be a carbohydrate such as a copolymer of cellulose and starch. An example of a commercially available carbohydrate absorbent is manufactured by Hoersct Celenese, Inc. The absorbate used with this type of absorbent is water. It has been found that this carbohydrate absorbent has the ability to absorb more than 100 times its weight in water. Another example of a carbohydrate absorbent is agar wherein the absorbate is water. The absorbent can also be a protein such as a polyamino acid. An example of a commercially available polyamino acid is manufactured by Mitsui Toatsu Chemicals, Inc. The absorbate used with a polyamino acid material is water. Another example of a protein absorbent is a gelatin wherein the absorbate is water. The absorbent can also be a fat. The absorbate for this type of material would be a nonionic, lipophilic fluid, such as an oil. It should be understood that a variety of organic absorbents and absorbates can be used in the present invention.

Figure 4:
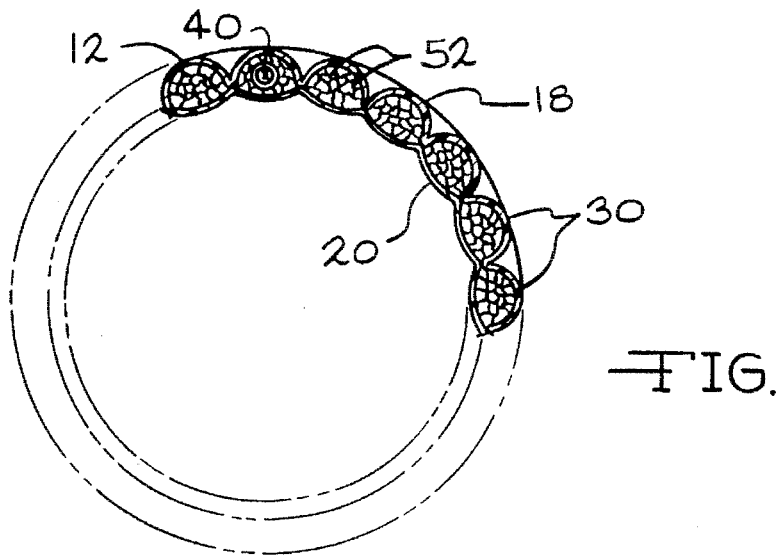
FIG. 4 is a cross-sectional view similar to the view of FIG. 3 showing the absorbent after absorption of the absorbate.

Referring to FIGS. 3–6, the implantation of the grafting stent 10 of the present invention will be described. When the grafting stent 10 has been positioned in a blood vessel at the site of implantation, the absorbate, such as water 50 is introduced through the opening 40 and into the chamber 32 and cylinders 30. The water 50 causes the chamber 32 and cylinders 30 to expand. The absorbent, such as a carbohydrate 52, absorbs the absorbate and increases in volume in the chamber 32 and cylinders 30. The one-way check valve 42 prevents the water 50 and carbohydrate absorbent 52 from escaping to the exterior of the tube member 12. As shown in FIGS. 4 and 6, the carbohydrate absorbent 52 completely absorbs the water 50. The carbohydrate absorbent 52 supports and maintains the expanded grafting stent 10 at the site of implantation.

The present invention can be modified and changed in a variety of ways with the scope of the invention being defined by the appended claims.

I claim:

1. An intraluminal stenting graft for implantation in a blood vessel, comprising:

a collapsible tube member having a first end and a second end, an outer layer and an inner layer extending between said ends, said outer layer being joined along a plurality of longitudinally extending lines to said inner layer to form a plurality of cylinders between said inner layer and said outer layer extending longitudinally between said first end and said second end, said cylinders, when expanded, providing structural support to said tube member, said tube member including means for introducing an absorbate therein; and an absorbent positioned in at least one of said cylinders, whereby when said absorbate is introduced to said plurality of cylinders and said absorbent, said absorbent absorbs said absorbate and increases in volume to support said tube member in said blood vessel.

2. The intraluminal stenting graft of claim 1, wherein said collapsible tube member further includes a first end wall extending between said outer layer and said inner layer at said first end and a second end wall extending between said outer layer and said inner layer at said second end.

3. The intraluminal stenting graft of claim 2, wherein one of said end walls includes said means for introducing an absorbate consisting of an opening therethrough.

4. The intraluminal stenting graft of claim 3, wherein said stenting graft further includes a one-way valve positioned in said opening to allow for the introduction of said absorbate into said tube member and to prevent the escape of said absorbent and said absorbate from said tube member.

5. The intraluminal stenting graft of claim 1, wherein said inner and outer layers are comprised of a biocompatible polymer material.

6. The intraluminal stenting graft of claim 1, wherein said outer layer is more flexible than said inner layer.

7. The intraluminal stenting graft of claim 1, wherein said absorbent is a carbohydrate.

8. The intraluminal stenting graft of claim 7, wherein said carbohydrate is a copolymer of cellulose and starch.

9. The intraluminal stenting graft of claim 7, wherein said carbohydrate is agar.

10. The intraluminal stenting graft of claim 1, wherein said absorbent is a protein.

11. The intraluminal stenting graft of claim 10, wherein said protein is a polyamino acid.

12. The intraluminal stenting graft of claim 10, wherein said protein is a gelatin.

13. The intraluminal stenting graft of claim 1, wherein said absorbent is a fat.

* * * * *